United States Patent [19]

Burton

[11] 4,389,418
[45] Jun. 21, 1983

[54] SKIN CARE COMPOSITION

[75] Inventor: Colin K. Burton, Racine County, Wis.

[73] Assignee: S. C. Johnson & Son, Inc., Racine, Wis.

[21] Appl. No.: 238,232

[22] Filed: Feb. 25, 1981

[51] Int. Cl.$^3$ .......................... A61K 7/00; A61K 7/48
[52] U.S. Cl. ..................................... 424/365; 424/358
[58] Field of Search .................. 424/70, 172, 358, 365

[56] References Cited

PUBLICATIONS

Soft Sense Label, 1981, S. C. Johnson & Son, Racine, WI 53403.
Balsam & Sagarin, Cosmetics, Sci. & Tech., Wiley-Intersci., NY, vol. I, 1972, pp. 59-63, 75, 126, 127, 134, 149, 193, 194, 203, 204, 213, 216, 217, 596, 597.

Primary Examiner—Anna P. Fagelson

[57] ABSTRACT

A skin care composition to moisturize and condition the skin with acceptable tactile properties includes a water-out emulsion of petrolatum or mineral oil, a quaternary ammonium emulsifier, a fatty alcohol and a fatty ester emollient. The composition provides the moisturizing and conditioning qualities of petrolatum, while providing a non-greasy, cosmetically acceptable feel when applied to the skin.

5 Claims, No Drawings

SKIN CARE COMPOSITION

BACKGROUND OF THE INVENTION

1. Field Of The Invention

This invention relates to an improved skin care composition for moisturizing and conditioning the skin. In particular, it relates to a cosmetically acceptable skin conditioning lotion or cream having an emulsified petrolatum or mineral oil base.

2. Description Of The Prior Art

Consumers have long desired a moisturizing and conditioning preparation in the form of a hand and body lotion or cream which, when applied, provides cosmetically acceptable tactile properties. The desirable properties of mineral oils and petrolatum have long been recognized primarily because of their beneficial effects on the skin. These ingredients are neutral, stable, odorless and substantially non-volatile at atmospheric conditions.

In particular, petrolatum has been used both alone, and as an ingredient in skin care products, for over 50 years. It is believed to be helpful in skin care, because it is occlusive and causes moisture to accumulate in the stratum corneum. Recently, A. M. Kligman, a respected research dermatologist, commented in a scientific paper titled "Regression Method For Assessing the Efficacy of Moisturizers" Cosmetics and Toiletries, Vol. 93, pages 27-35, Apr. 1, 1978, that when it comes to efficacy, petrolatum is the unrivaled moisturizer. Kligman reported that petrolatum is a tenacious substance which stays in place, filling in the irregularities and smoothing the surface (of the skin) for many hours. Kligman postulated that petrolatum and other effective greases, resist wear-off, reduce friction and roughness and perhaps, most importantly of all, contain substances which cross the horny layer barrier, altering the epidermis so that it does not desquamate abnormally, when the dew point is low.

Kligman believed that moisturizers have undisclosed pharmacologic effects on epidermal physiology. He further observed that:

"The creation of a moisturizer is still an art, a trial and error endeavor resting on a weak scientific foundation. One cannot sit at a desk and compose a superior moisturizer on rational principles unless of course aesthetics are ignored."

It has long been known that petrolatum is extremely difficult to formulate in a pleasing aesthetic state and, therefore, it is not present in many commercially available skin care products. Petrolatum or petroleum jelly, when applied to the skin, is greasy and cosmetically unacceptable. Attempts have been made to emulsify petrolatum in a cream or lotion form in order to reduce its greasy and unacceptable tactile properties, when applied to the skin. Petrolatum per se in lotion form is inherently unstable. In general, by adding conventional water-soluble detergent emulsifiers to stabilize the petrolatum or mineral oil, the moisturizing properties of the petrolatum are unacceptably reduced.

As employed herein the term "conditioning" relates to the deposition of a palpable emollient film on the skin, which works to retard the loss of moisture from the epithelium and to maintain or restore the softness and smoothness of the skin surface. As employed herein the term "moisturizing" relates to the formation of a cosmetically acceptable film on the skin which reduces transepidermal water loss (TEWL). A product "moisturizes" when water which is normally lost to the atmosphere is accumulated in the stratum corneum. This accumulation causes the skin to be moisturized.

A satisfactory skin care composition having superior moisturizing and conditioning properties with cosmetically acceptable tactile properties should exhibit satisfactory feel, lubricity and absorption when applied to the skin. In particular, the composition should exhibit good consistency, should apply evenly to the skin, should be absorbed rapidly and should dry quickly. After application, the skin should feel smooth and clean. The composition should assist in relieving the tight feeling of dry skin and should soothe irritated skin.

Until now, prior art and commercially available cosmetic formulations have failed to achieve all the aforementioned desired properties. In U.S. Pat. No. 3,818,105 there is disclosed a composition including cetyl alcohol, a fattyalkyl dimethylbenzyl ammonium compound and mineral oil in a skin lubricant formulation. Optional ingredients include an organic ester dispersion media, humectants, white oil and petrolatum.

U.S. Pat. No. 4,137,302 discloses cosmetic compositions containing emollients including cetyl alcohol, isopropyl palmitate and petrolatum. Various cationic emulsifiers are also disclosed.

U.S. Pat. No. 3,829,563 discloses petrolatum and fatty alcohols in a foaming detergent. U.S. Pat. No. 3,666,690 teaches a skin cleansing composition including mineral oil, a specific cationic surface active agent, a nonionic surface active agent, humectants and thickeners. Cosmetic compositions containing petroleum jelly in combination with the usual cosmetic ingredients are disclosed in U.S. Pat. Nos. 3,392,040, 3,609,102 and 3,981,990.

Recently, attempts have been made to improve skin care compositions with the introduction of such products as Wondra, Vaseline Intensive Care Lotion and Sensuously Silky. These products are subject to various defects. In general, the compositions provide a film which is palpably oily and greasy to the touch upon application. The applied films tend to be removed by water without much resistance and do not provide a level of moisturizing which is deemed cosmetically acceptable to users.

SUMMARY OF THE INVENTION

It is, therefore, an object of the present invention to provide a skin care composition free of the defects and deficiencies of the prior art which provides enhanced moisturizing and conditioning properties while exhibiting cosmetically acceptable tactile properties.

These and other objects are attained in a skin care composition for moisturizing and conditioning the skin having cosmetically acceptable tactile properties which comprises a water-out emulsion comprising (a) petrolatum or a mineral oil in sufficient amounts to moisturize and condition the skin; (b) a quaternary ammonium compound of the formula:

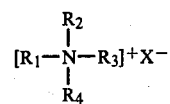

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt forming anion in sufficient amounts to emulsify said petrolatum or mineral oil and to condition the skin; (c) a fatty alcohol in sufficient amounts to stabilize the emulsion and to provide a cosmetically acceptable viscosity therefor; and (d) a fatty ester emollient in sufficient amounts to enhance the tactile properties of said composition.

A significant feature of the present invention resides in the use of a di-lower alkyl, di-higher alkyl, ammonium emulsifying agent for the oils employed in the present invention. This cationic surfactant is the primary emulsifier and is believed to also soften and protect the skin. Although the cationic surfactant emulsifies oils in water to form the product, when the aqueous phase evaporates upon application to the skin, the cationic assists in forming a water-repellant layer on the skin.

The composition of the present invention has been formulated to achieve total aesthetic properties for the product. The present compositions provide enhanced cosmetic properties, lubricity, rapid absorption and also contribute to the water repellancy of the total residual layer left on the skin after application. The present composition overcomes the otherwise unacceptable greasy feel of the petrolatum and mineral oil to provide a product with enhanced moisturizing and conditioning properties.

Prior art skin conditioning lotions employing water-soluble detergent surfactants as emulsifiers, such as triethanolamine stearate, polyethylene glycol (100) stearate and the like, do not provide effective skin moisturizing. These conventional water soluble surfactants generally produce a product which is unacceptably oily and greasy to the touch after application. In addition the product films are readily removed upon application of water.

DESCRIPTION OF PREFERRED EMBODIMENTS

The petrolatum suitable for use in the present invention comprises any grade of white or yellow petrolatum which is recognized as being safe for application to the human skin. The preferred types are petrolatum U.S.P. XVIII or NFXII. In general, any viscosity or consistency grade of petrolatum recognized in the art can be employed in the present invention. It is within the scope of the invention to partially replace petrolatum with mixtures of hydrocarbon materials which can be formulated to resemble petrolatum in appearance and consistency. For example, such a combination can be formed by melting mineral oil in various proportions with substances such as, for example, microcrystalline wax, paraffin wax and the like.

The mineral oil employed in the present invention should be USP or NF grade white mineral oils and should have a viscosity of 6.7 to 69 cst at 40° C., a specific gravity (SG 15.6° C./15.6° C.) of 0.828 to 0.890 and a maximum pour point of $-18°$ to $-7°$ C. Preferred mineral oils should have a viscosity of 6.7 to 17.0 cst at 40° C., a specific gravity of 0.828 to 0.860 and a maximum pour point of about $-7°$ to $-10°$ C.

The quaternary ammonium emulsifiers of the present invention have the general formula:

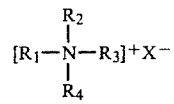

wherein $R_1$ and $R_2$ are each long chain, substantially linear alkyl groups having from about 16 to 22 carbon atoms, $R_3$ and $R_4$ are each lower alkyl groups of from about 1 to 3 carbon atoms, and X is a salt-forming anion. Preferably the salt forming anion is chloride, bromide, or iodide. The cationic emulsifiers preferably exhibit hard, waxy and nonsticky characteristics.

In general, when long chain alkyl groups below $C_{16}$, ethoxylated cationics or mono long chain alkyl groups are employed, the viscosity of the resulting formulation is reduced to an unacceptable level. In addition to its emulsifying properties, skin softening and skin protective properties, the quaternary is believed to provide still another unique feature upon application to the skin.

As a cationic surfactant, the quaternary emulsifier carries a positive charge. In general, detergents and soaps are anionic and carry negative charges. When the cationic emulsifier comes into contact with residual soaps and detergents on the skin, an insoluble complex is formed. While uncomplexed, the residual soap and detergent can induce irritation. Application of the cationic emulsifier should prevent this residual irritation from occurring.

The most preferred quaternary emulsifier is dimethyl distearyl ammonium chloride.

The fatty alcohol employed in the present invention assists in stabilizing the emulsion and in providing a cosmetically acceptable viscosity for the composition. In general, a $C_{14}$ to $C_{22}$ substantially saturated alkanol is employed. Typical examples of suitable fatty alcohols include stearyl alcohol, myristyl alcohol, behenyl alcohol, arachidic alcohol, isostearyl alcohol and isocetyl alcohol. Enhanced results are obtained and accordingly, it is preferred, to employ cetyl alcohol. If desired, cetyl alcohol may be employed alone or in combination with other fatty alcohols, particularly, isostearyl alcohol.

The fatty ester emollient of the invention is employed in sufficient amounts to enhance the tactile properties of the composition. In particular, the fatty esters assist in softening the base formulation of petrolatum, quaternary emulsifier and fatty alcohol. Typical fatty esters employed in the present invention include isopropyl myristate, isopropyl palmitate, isopropyl isostearate, isostearyl isostearate, diisopropyl sebacate, propylene glycol dipelargonate, 2-ethylhexyl isononoate, 2-ethylhexyl stearate, $C_{12}$–$C_{16}$ fatty alcohol lactate, isopropyl lanolate, 2-ethyl-hexyl salicylate and mixtures thereof. The preferred fatty ester is isopropyl palmitate.

The amount of water or aqueous vehicle to be included in the compositions of the invention varies depending upon the desired consistency of the final product. Since the compositions of the invention are oil-in-water emulsions, it is possible by varying the amount of water present to formulate, for example, a thick-flowing liquid or lotion, a semi-liquid thick cream, a paste and the like. Deionized water is preferably employed as the aqueous vehicle.

If desired, a humectant may be present in the compositions of the invention. It has been postulated that humectants can be entrapped in the interstices of the surface stratum corneum, where they act as a hygroscopic agent, thus increasing the amount of water held in this area. The water is given up by the humectant, as required, to contribute to the softening of the skin surface. Typical humectants employed in the present invention are propylene glycol, sorbitol, polyethylene glycol and the like and mixtures thereof. Such humectants can be employed in addition to or substituted partially for, the deionized water.

A particularly preferred humectant is glycerin which, apart from its water binding properties, is postulated to also visually improve the surface of dry skin.

In order to improve the lubricity of the composition during application it is desirable to employ a silicone oil or fluid, such as a dimethylpolysiloxane or other conventional polysiloxane. In general, the viscosity of the silicone oil at a temperature of 25° C. is from about 5 centistokes to 12,500 centistokes. Typical polysiloxanes employed in the invention include dimethylpolysiloxane, (CTFA name-dimethicone, a dimethyl polysiloxane endblocked with trimethyl units), diethylpolysiloxane, dimethylpolysiloxane-diphenylpolysiloxane, cyclomethicone, trimethylpolysiloxane, diphenylpolysiloxane, and mixtures thereof.

Best results are obtained with dimethylpolysiloxane, having a viscosity of between 10 and 1,000 centistokes.

Other conventional additives typically employed in cosmetic compositions may be utilized. Fragrance oils, which mask the odor of the base and provide cosmetic appeal, can be employed. Nontoxic and compatible dyes may be utilized to color the composition, as desired. Preservatives, such as methylparaben or other esters of parahydroxy benzoic acid, can be employed. If desired, formaldehyde and like preservatives can also be utilized. Additionally, minor amounts of other conventional emollients, emulsifiers, thickeners or other cosmetic additives can be employed.

In addition, other ingredients can be employed beneficially to provide a specifically tailored cosmetic composition. For example, a sun screen additive, such as octyl dimethyl para-aminobenzoic acid can be employed in the inventive composition in amounts from about 1% to 8% by weight of the total composition. To provide a skin protectant composition, zinc oxide and like ingredients can be provided in amounts from about 0.5% to 3% by weight of the composition. As a medicament, various essential oils, such as menthol and the like, can be employed in amounts from 0.1% to 2% by weight of the composition.

As employed herein the percentages of ingredients are by weight of total composition, unless otherwise indicated. The compositions of the invention, in general, comprise from about 1% to 10%, preferably from about 1% to 6% petrolatum or mineral oil; from about 2% to 12%, preferably from about 2% to 7% cationic emulsifier; from about 1.5% to 5%, preferably from about 1.5% to 3.0% fatty alcohol; from about 1% to 8%, preferably from about 1% to 5% of fatty ester; and the balance, aqueous vehicle, preferably deionized water.

Generally, the compositions of the invention should not contain less than about 25% and no more than about 50% of water if a cream composition is desired, and not less than about 75% and no more than about 95% of water where a lotion or liquid form is desired. The preferred form is a lotion having from about 75% to 85% water.

In general, the amounts of humectant employed are from about 0 to 10%, preferably from about 2% to 7%; the amount of silicone oils employed is from about 0 to 5% and preferably from about 0.1 to 1%; the quantity of fragrance employed is from about 0.005% to 2%, preferably from about 0.01% to 0.2% and the amount of preservative is preferably from about 0.1% to 0.2%.

In general, the total nonvolatiles in the composition of the invention can vary from about 8% to 50% and is preferably from about 15% to 25% by weight of the composition.

The compositions of the invention are prepared, generally, by dispersing the fatty alcohol and cationic emulsifier into the petrolatum or mineral oil. The resulting dispersion is heated to a temperature of from about 170° F. to 190° under agitation to form a hot oil phase. The aqueous vehicle, colorant and preservative are admixed and heated to a temperature of from about 170° F. to 190° under agitation to form a hot aqueous phase. Next, the hot oil phase is added to the hot aqueous phase and the resulting dispersion is agitated until a homogeneous mixture is obtained.

The mixture is then cooled to a temperature of about 90° F. and fragrance is added under agitation until a homogeneous product is obtained. Depending upon the quantity of aqueous vehicle employed, a homogeneous lotion or cream is produced.

The skin care compositions of the present invention are topically applied in a conventional manner. In general, the compositions may be dispensed from a container and then gently applied to the skin. The compositions are rapidly absorbed and leave the skin with a soft and smooth appearance.

The following Examples serve to further illustrate certain preferred embodiments of the present invention and are not limitative of scope:

EXAMPLE 1

A skin care composition of the invention is prepared as follows:

Into a jacketed kettle is charged 25% of the deionized water employed in the formulation. Thereafter, dimethyl distearyl ammonium chloride, petrolatum, cetyl alcohol, isopropyl palmitate, Dimethicone (dimethyl polysiloxane fluid, supplied as Dow Corning-DC 225 fluid), methyl and propyl paraben preservatives and glycerin is added. The mixture is slowly heated to a temperature between about 180° F. and 190° F. while agitating the mix with sufficient shear and turnover to obtain a homogeneous mixture. Agitation is continued for about 30 minutes.

Thereafter, the remaining water, at an addition temperature from about 50° F. to 70° F., is added slowly under continuous and increasing agitation. After all the water is added, the mixture has a resulting temperature of from 90° F. to 110° F. The perfume is thereafter added under agitation until a homogeneous lotion is produced.

The resulting skin care product is applied to the skin as needed to alleviate the symptoms of dry skin.

The skin care composition thus formed has the following ingredients:

| Ingredients | Weight Percent |
|---|---|
| Dimethyl distearyl ammonium chloride* | 5.0 |
| Petrolatum, U.S.P. | 4.0 |
| Glycerin | 4.0 |

-continued

| Ingredients | Weight Percent |
| --- | --- |
| Isopropyl palmitate | 3.0 |
| Cetyl alcohol | 2.0 |
| Dimethicone (10 cst) | 0.25 |
| Fragrance | 0.05 |
| Paraben preservatives | 0.14 |
| Deionized water | 81.56 |
| Total | 100.00 |

*Tradename – Quaternium-5, supplied by Sherex Chemical as Arosurf TA-100

EXAMPLE 2

A skin care lotion was prepared substantially in accordance with the procedures set forth in Example 1 having the following composition:

| Ingredients | Weight Percent |
| --- | --- |
| Petrolatum, U.S.P. | 4.0 |
| Dimethyl distearyl ammonium chloride | 4.0 |
| Cetyl alcohol, N.F. | 1.50 |
| Isostearyl alcohol | 1.0 |
| Glycerin, U.S.P. | 4.0 |
| Isopropyl palmitate | 2.0 |
| Dimethicone (1000 cts) | 1.0 |
| Methyl p-hydroxybenzoate | 0.10 |
| Propyl p-hydroxybenzoate | 0.04 |
| Fragrance | 0.05 |
| Deionized water | 82.31 |
| Total: | 100.00 |

EXAMPLE 3

In order to assess the moisturizing effect of the compositions of the present invention three lotion formulations designated A, B and C were prepared in accordance with the procedures substantially as set forth in Example 1. The formulations are as follows:

| Ingredients | Weight Percent A | B | C |
| --- | --- | --- | --- |
| Mineral oil, N.F, | 0.0 | 0.0 | 4.0 |
| Petrolatum, U.S.P. | 4.0 | 4.0 | 0.0 |
| Dimethyl distearyl ammonium chloride | 4.0 | 4.0 | 4.0 |
| Cetyl alcohol | 1.5 | 1.5 | 1.5 |
| Isostearyl alcohol | 1.0 | 1.0 | 1.0 |
| Glycerin, U.S.P. | 4.0 | 0.0 | 4.0 |
| Isopropyl palmitate | 2.0 | 2.0 | 2.0 |
| Dimethicone (1000 cst) | 1.0 | 1.0 | 1.0 |
| Methyl p-hydroxybenzoate | 0.1 | 0.1 | 0.1 |
| Propyl p-hydroxybenzoate | 0.04 | 0.04 | 0.04 |
| Deionized Water and fragrance | 82.35 | 86.35 | 82.35 |
| TOTAL | 100.00 | 100.00 | 100.00 |

The compositions designated A, B and C were tested against petrolatum, itself, and a commercially available skin lotion identified as Wondra Skin Conditioning Lotion, supplied by Proctor and Gamble, hereinafter referred to as PG and having the following approximate formulation:

PG

Triethanolamine stearates (emulsifier), ethoxylated fatty ester, Carbopol (thickener), mineral oil, fatty alcohol, sorbitol (humectant), isopropyl saturated fatty ester, glyceryl stearate, preservatives, titanium dioxide, water and silicone oil.

In addition, a control was run in which untreated skin was passed through the test procedure and the results measured. To assess the moisturizing effect of the various formulations, 0.02 milliliters of each composition was applied to a respective forearm site in nine female subjects. The transepidermal water loss ("TEWL") of each site was measured with a Servo-Med evaporimeter, ½ hour after application of each composition. The compositions were then partially removed from the sites by wiping twice with Kim-wipes and the measurements thereafter taken. The skin temperatures were also recorded. A randomized block analysis of variance was performed on all the data generated by the test formulations where the compound was present on the skin.

A significant difference of TEWL was observed with when employing the randomized block analysis of variance. Multiple range analysis indicated that formulations A, B, C and petrolatum could be lumped together as occlusive substances, whereas formulation PG, similar to the control, appeared to produce no occlusion.

A Newman-Keuls multiple range analysis showing the TEWL measured in $gm^{-2} hr^{-1}$, is presented in Table 1 as follows:

TABLE 1

| Formulation | TEWL Value $gm^{-2} hr^{-1}$ |
| --- | --- |
| A | 2.2 |
| B | 2.7 |
| C | 2.9 |
| Petrolatum | 3.0 |
| PG | 3.8 |
| Control | 4.1 |

The data reflects the superiority of the compositions of the invention and their unexpectedly superior moisturizing properties in comparison to a commercially available composition. The results indicate that transepidermal water loss was significantly reduced by the compositions of the invention, to a level similar to petrolatum, alone, although the inventive compositions contain petrolatum in an emulsified form. The results also demonstrate that, when compositions employing mineral oil in lieu of petrolatum are employed, formulations are provided which exhibit satisfactory moisturizing properties, even as compared to petrolatum employed alone.

EXAMPLE 4

In order to further demonstrate the moisturizing properties imparted to skin by the present invention, the following formulations of the invention were prepared in accordance with the procedures set forth in Example 1:

| Ingredients | Weight Percent D | E |
| --- | --- | --- |
| Dimethyl distearyl ammonium chloride | 5.0 | 5.0 |
| Petrolatum | 4.0 | 3.0 |
| Glycerin | 4.0 | 6.0 |
| Isopropyl palmitate | 3.0 | 3.0 |
| Cetyl alcohol | 2.0 | 2.5 |
| Dimethicone | 0.25 | 0.25 |
| Fragrance | 0.05 | 0.05 |
| Paraben preservatives | 0.02 | 0.02 |
| Deionized water | 81.68 | 80.18 |
| Total: | 100.00 | 100.00 |

Three commercially available formulations were also employed in this test. The first commercially available formulation tested was Vaseline Intensive Care Lotion supplied by Cheseborough-Ponds, hereinafter referred to as CP. The second formulation is an oil-in-water cream supplied by American Hoechst and identified hereinafter by the designation Nr. La 469/4. The final formulation was Wondra Skin Conditioning Lotion, PG, as set forth in Example 3. The formulation of the commercial compositions is as follows:

| Nr. La 469/4 | Weight Percent |
|---|---|
| Dimethyl distearyl ammonium chloride | 5.0 |
| Petrolatum | 8.0 |
| Isopropyl myristate | 7.0 |
| Glycerin | 3.0 |
| Fatty acid ester | 7.0 |
| Wax | 5.0 |
| Beeswax | 3.0 |
| Water, preservative, perfume oil | 62.0 |

| CP | Weight Percent* |
|---|---|
| Mineral oil | 4.0 |
| Cetyl alcohol | 0.3 |
| Propylene glycol | 0.2 |
| Glycerin | 10.0 |
| Triethanolamine stearate (emulsifier) | 4.2 |
| Acetylated lanolin alcohol | 0.7 |
| Thickener | 0.2 |
| Glyceryl stearate | 0.5 |
| Glycol stearate | 1.2 |
| Water, dyes, perfume, preservative | Balance |

*The weight percentages are approximations for CP.

An in-vitro test was carried out to characterize the films for their capacity to reduce trans-film moisture loss through semipermeable films or membranes.

The test system employed capacitive-type sensors for recording the temperature and relative humidity of heated, dry nitrogen gas crossing a dialysis membrane in a modified Franz diffusion cell. Low gas pressures, on the order of 10 psi, and low flow rates, less than about 50 cubic centimeters per minute, were employed to approximate laminar flow across the membrane surface of skin. Uniform temperatures on both sides of the membrane were maintained by means of circulating water jackets on the diffusion cell. All products were flow coated onto half of the dialysis membrane. The remaining half of the membrane served as a control.

All measurements were taken until a steady state water loss was observed. The percent reduction was calculated by the equation:

% Reduction = $\left[ \dfrac{\text{(water loss untreated} - \text{water loss treated)}}{\text{(Water loss untreated)}} \right] \times 100$ The results of the experiment are reported in Table 2 as follows:

TABLE 2

| Formulation | % Reduction |
|---|---|
| Composition D | 34 |
| Composition E | 23 |
| Nr. La 469/4 | 1 |
| CP | 27 |
| PG | 16 |

Formulation Nr. La 469/4 does not contain a fatty alcohol, such as cetyl alcohol. Formulation PG employs a water soluble detergent as an emulsifier, as contrasted with the cationic emulsifier of the present invention. Formulation CP was absorbed more slowly than the inventive formulations and, after application, exhibited a cosmetically unacceptable greasy feel. In addition, Formulation CP is more easily removed upon contact with water than the formulations of the present invention. Additionally, formulation CP employs a detergent emulsifier as contrasted with the cationic emulsifier of the present invention.

EXAMPLE 5

A cosmetic comparison for tactile properties was conducted between a skin care composition of the present invention prepared substantially in accordance with the procedure of Example 1 and a commercially available conditioner, Sensuously Silky supplied by Alberto Culver Co. The label formulation of the commercially available conditioner is as follows:

Formulation

Mineral Oil, Quat 18, Quat 19, isopropyl palmitate, cetyl alcohol, propylene glycol, Dimethicone, PEG (100) stearate, lanolin alcohol, glycerol stearate, sodium lactate, water, preservative, fragrance and $TiO_2$.

The primary emulsifier for the commercially available skin conditioner, polyethylene glycol (100) stearate, is a water soluble surfactant. It is believed that about 1.5 percent of a quaternary ammonium surfactant, Quat 18, is also present.

After application to the skin, the commercially available conditioner leaves an oily and greasy residue, which is cosmetically unacceptable to the user. In addition, owing to the use of the water soluble surfactant as the primary emulsifier, the film is more easily dispersed as compared to the compositions of the present invention. In contrast, the inventive compositions are readily absorbed and moisturize dry skin without leaving a greasy, cosmetically unacceptable residue.

While various preferred embodiments of the present invention have been illustrated by means of specific examples, it is to be understood that the present invention is in no way to be deemed as limited thereto, but should be construed as broadly as all, or any equivalent thereof.

Wherefore, I claim:

1. A skin care composition for moisturizing and conditioning the skin having cosmetically acceptable tactile properties which comprises a water-out emulsion consisting essentially of:

(a) From about 1 to 10% by weight of petrolatum or mineral oil;

(b) From about 2 to 12% by weight of a quaternary ammonium compound of the formula

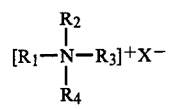

wherein $R_1$ and $R_2$ are each long chain, substantially linear alkyl groups having from about 16 to 22 carbon atoms, $R_3$ and $R_4$ are each lower alkyl groups having from about 1 to 3 carbon atoms and X is a salt-forming anion;

(c) From about 1.5 to 5% by weight of a fatty alcohol;

(d) From about 1 to 8% by weight of a fatty ester emollient; and
(e) From about 75 to 95% by weight aqueous vehicle.

2. The composition of claim 1 wherein the composition includes from 0 to about 10% by weight of a humectant.

3. The composition of claim 1 which further includes from 0 to 5% of a silicone oil or fluid having a viscosity of from 5 to 12,500 centistokes.

4. The composition of claim 3 in which the skin care composition is a lotion comprising a water-out emulsion containing from about 75% to 85% of an water, from about 1% to 6% petrolatum, from about 2% to 7% of dimethyl distearyl ammonium chloride, from about 1% to 5% isopropyl palmitate, from about 1.5% to 5% cetyl alcohol, and from about 0.1% to about 1.0% of a dimethyl polysiloxane fluid having a viscosity from about 10 to 1,000 centistokes.

5. The composition of claim 1 wherein the aqueous vehicle is a mixture of humectant and water.

* * * * *